(12) United States Patent
Fuisz

(10) Patent No.: US 6,337,083 B1
(45) Date of Patent: Jan. 8, 2002

(54) ORAL DELIVERY METHOD AND COMPOSITION FOR SOLID MEDICATIONS OR DIETARY SUPPLEMENTS

(75) Inventor: Richard C. Fuisz, McLean, VA (US)

(73) Assignee: International Fluidics, Great Falls, VA (US)

(*) Notice: Subject to any disclaimer, the term of this patent is extended or adjusted under 35 U.S.C. 154(b) by 0 days.

(21) Appl. No.: 09/672,949

(22) Filed: Sep. 29, 2000

Related U.S. Application Data

(60) Provisional application No. 60/194,592, filed on Apr. 5, 2000.

(51) Int. Cl.[7] .............................. A61K 9/08; A61K 9/20; A61K 9/48

(52) U.S. Cl. ...................... 424/439; 424/464; 424/466; 424/451

(58) Field of Search ................................ 424/466, 464, 424/439, 451

(56) References Cited

U.S. PATENT DOCUMENTS 5,670,168 A * 9/1997 Baichwal et al. ........... 424/464
6,143,276 A * 11/2000 Unger ........................ 424/9.3

OTHER PUBLICATIONS

Am J of Gastroenterology, vol. 94, No. 7, Virender K. Sharma, M.D. et al, Oct. 1998.*

Database CAPLUS on STN, AN 1996:565491. JONES, R. et al. "Kapanol capsules: Peller formulation provides alternative methods of administration of sustained–release morphine sulfate". Clinical Drug Investigation. 1996, vol. 12, No. 2, pp. 88–93, whole Abstract.

* cited by examiner

Primary Examiner—Diana Dudash
Assistant Examiner—Mina Haghighatian
(74) Attorney, Agent, or Firm—Antonelli, Terry, Stout & Kraus, LLP

(57) ABSTRACT

An oral delivery composition and method are provided for facilitating the swallowing of a solid object such as a pill, tablet, capsule or caplet. The oral delivery composition is made up of a mixture of a base liquid and at least one additive. The additive is selected and is present in the oral delivery composition in a sufficient concentration such that the oral delivery composition has improved physical properties, in comparison with the base liquid, so that when the oral delivery composition and a solid object to be swallowed by a user are administered together to the user and swallowed, the solid object is less likely to become lodged or stuck on tongue, throat, palate or esophageal surfaces of the user, in comparison to when the base liquid and the solid object are administered together and swallowed.

39 Claims, 1 Drawing Sheet

ORAL DELIVERY METHOD AND COMPOSITION FOR SOLID MEDICATIONS OR DIETARY SUPPLEMENTS

CROSS REFERENCE TO RELATED APPLICATIONS

This application claims priority from Provisional Application Ser. No. 60/194,592, filed Apr. 5, 2000.

BACKGROUND OF THE INVENTION

The invention relates to oral delivery compositions and methods to facilitate the swallowing of solid objects such as pills, tablets, caplets, capsules and solid food.

Solid oral medications and dietary supplements, and other solid materials taken orally in the form of pills, capsules and tablets are typically placed in the mouth and swallowed with a mouthful of water or other beverage. It has been estimated that more than one quarter of the population perceives that they have difficulty swallowing these solid materials such as oral medications and dietary supplements that are in the form of capsules and tablets. Just as a boat in shallow water can ground itself, so can a tablet or capsule ground itself on the tongue and make swallowing difficult. Further, even after a tablet or capsule is swallowed, it can cause discomfort as it travels down the esophagus.

One reason that swallowing a tablet or capsule can be difficult is that when a tablet or capsule is exposed to ordinary fluids such as water or juice, it becomes sticky. This problem may be illustrated by a simple experiment of placing a tablet or capsule in an elongated beaker, adding a small amount of water, and inverting the beaker. In many cases, the tablet or capsule will stick to the side of the beaker instead of flowing out with the fluid.

Attempts to make tablets easier to swallow by, for example, coating them with a gelatinous coating do not completely solve the problem, and may even make the problem worse. Most of the coatings that are commonly used, by virtue of their "gelatinous" nature, begin to soften or dissolve in the mouth. This can cause a coated tablet to stick to the tongue if it is not immediately swallowed, and any hesitation can make swallowing thereafter even more difficult than if the tablet were not coated.

More recently, attempts to provide medications that are more easily swallowed have been directed toward "quick dissolve tablets", that is, medications that are stored in tablet form but that disintegrate in the mouth. A drawback of this approach is that a dissolved medication becomes more exposed to mouth and throat surfaces, exposing the user to the bitter taste of the medication, which may be difficult to mask. Further, many medications have a harmful effect on the teeth, gingiva and throat and mouth surfaces. Therefore, prolonged exposure of these surfaces to a dissolved medication, which can occur if the dissolved medication is not completely swallowed or washed out of the mouth each time, is undesirable. Also, providing medications in the form of quick dissolve tablets tends to add significantly to the cost of the medication.

Many solid materials that are taken orally, such as medications and food supplements, come in the form of elongated capsules, pill, caplets or tablets. This dosage form presents a further problem in swallowing because in the mouth of the user, the elongated capsule, pill or tablet can become oriented transversely in relation to the passage down the throat (a situation analogous to that of a canoe sitting sideways in a narrow, swift-flowing river), still further increasing the tendency of the solid material, such as a medication or food supplement, to become grounded or lodged in the throat or esophagus. Water and juice are typically unable to provide sufficient force, coupled with wetting, lubrication and viscosity to straighten out the elongated capsule, pill or tablet and to prevent the lodging or grounding.

Moreover, there are certain people who, because of age or medical conditions, have difficulty in swallowing solid food, even when the food is taken with water or juice.

SUMMARY OF THE INVENTION

Accordingly, it is an object of the present invention to provide an oral delivery composition that facilitates the swallowing of a solid object such as a pill, capsule or tablet or solid food.

It is further object of the present invention to provide a method for swallowing a solid object such as a pill, capsule, tablet, caplet or solid food.

It is a further object of the present invention to provide an oral delivery composition that, when ingested with a solid object such as a pill, capsule, caplet or tablet or solid food, encapsulates and buoys the pill, capsule, caplet or tablet or solid food so that the pill, capsule, caplet or tablet or solid food is swallowed without becoming lodged or grounded on surfaces in the mouth or esophagus of the user.

It is a further object of the present invention to provide an oral delivery composition that facilitates the swallowing of elongated pills, capsules, caplets or tablets.

These and other objects are accomplished by providing an oral delivery composition made up of a base liquid and one or more additives, wherein the one or more additives are selected and are present in the oral delivery composition in a sufficient concentration such that the oral delivery composition has improved physical properties, in comparison with the base liquid by itself, such that when the oral delivery composition and the solid object are administered together to a user and swallowed, the solid object is less likely to become lodged or stuck on tongue, throat, palate or esophageal surfaces of the user, in comparison to when the base liquid and the solid object are administered together and swallowed. In particular, the additive or additives are selected to give the oral delivery composition at least one of the following properties:

(1) a density that is greater than the density of the base liquid, (2) a surface tension that is less than the surface tension of the base liquid, (3) a viscosity that is greater than the viscosity of the base liquid, (4) a wettability that is greater that the wettability of the base liquid, (5) a lubricity that is greater than the lubricity of the base liquid, and (6) interfacial tension that is less than that of the base liquid.

The present invention is further directed to an additive composition that can be added to a base liquid to provide improved properties, such as those listed above, to facilitate the swallowing of a solid object.

The present invention is further directed to methods of swallowing of a solid object such as a pill, capsule, caplet or tablet or solid food by administering the solid object together with the oral delivery composition.

DETAILED DESCRIPTION OF THE PREFERRED EMBODIMENT

Figure 1:
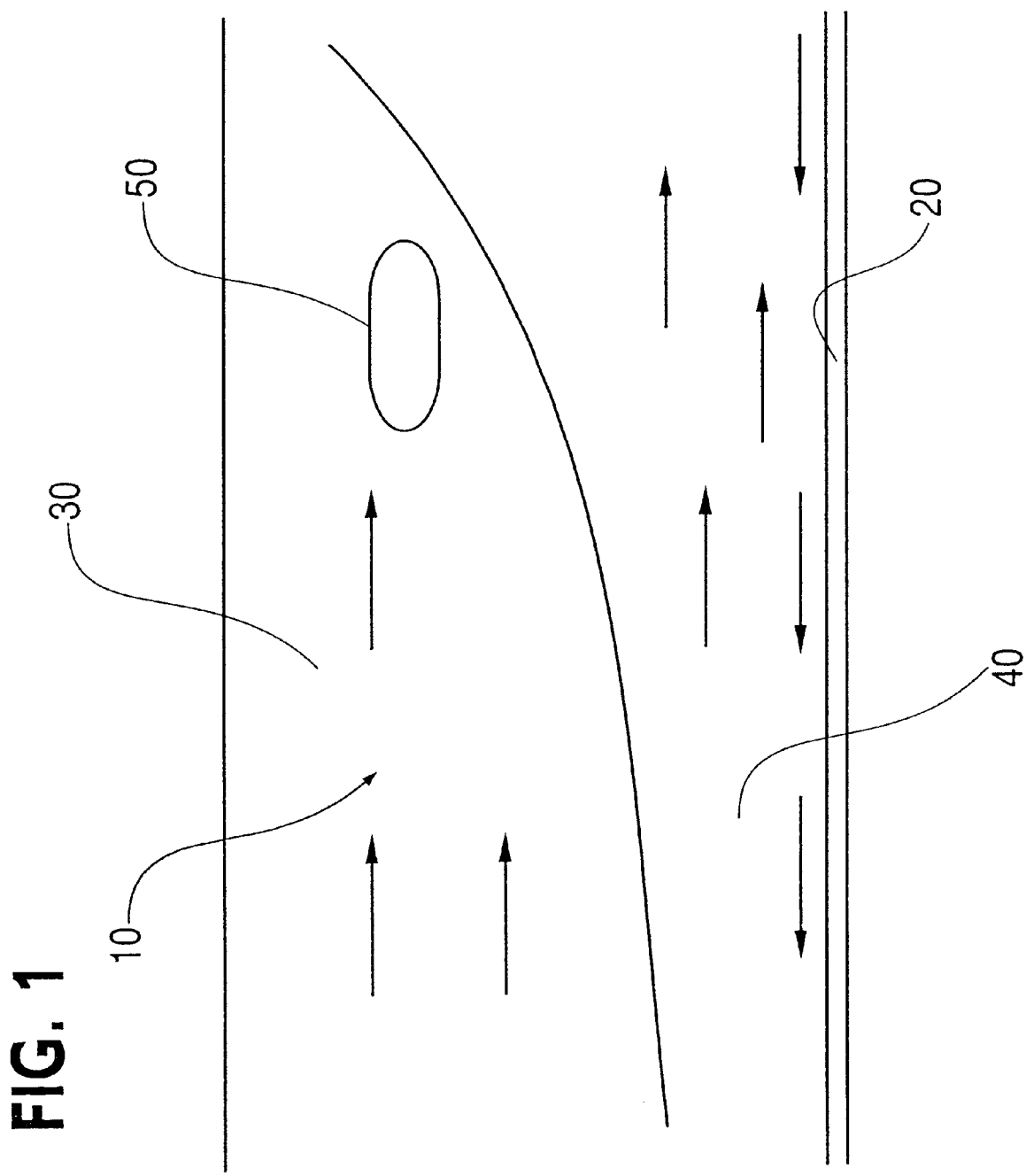
FIG. 1 is a schematic depiction of the forces acting on a tablet or other solid object that is moving in a fluid close to a surface.

Swallowing is a complex transient flow process occurring in a brief time interval. When a solid object such as a tablet or capsule is swallowed, the rigid solid object moves against a deformable body cavity. The solid object must traverse an irregular flow channel, including the buccal cavity and the esophagus, encountering varying shear rates and channel dimensions as it purges through the esophagus.

It has been determined that water is not the best medium for swallowing solid objects such as pills, capsules, tablets, caplets or solid food. The reason is that the physical properties of water, such as density, surface tension, interfacial tension (including wettability), viscosity, and lubricity, do not prevent the solid object from becoming grounded on the tongue or from sticking to surfaces of the mouth. (Typically, other common substances such as juice are not an improvement.)

According to the present invention, the problem is solved by providing an oral delivery composition having improved physical properties or suspension properties in comparison with water or juice. The improved physical properties include at least one of greater density, lesser surface tension, lower interfacial tension (and therefore increased wettability), greater viscosity and greater lubricity. The oral delivery composition is obtained by providing an additive or a combination of additives that provide the enhanced physical properties when combined with a base liquid such as water or juice.

Without limiting the invention to any particular theory, it is postulated that increased wetting and viscosity of a liquid aids in the swallowing of a solid object by providing buoyancy. Increased wettability of a liquid aids in swallowing of the solid object by pulling the solid object into the bulk of the liquid. Once the solid object is engulfed in the liquid, the viscosity of the liquid carries the solid object along on a barrier layer thereby allowing the solid object to float and not become grounded on the surface of the throat, tongue or esophagus.

Decreased surface tension and increased wettability of a liquid aid in the swallowing of a solid object by enhancing the ability of the liquid to wet the surfaces of a solid object, such as hydrophobic surfaces of a tablet, thereby altering the adhesiveness or sticking properties of the surfaces of the solid object. Decreased surface tension and decreased interfacial tension (and therefore increased wettability) further enhance the ability of the liquid to envelop or encapsulate a solid object so that surfaces of the solid object do not come into contact with surfaces of the mouth, tongue, throat or esophagus. Therefore, in its most fundamental form, the invention relates to a composition and method for wetting a solid object that is exposed to or is resting on or against a non-moving surface, so that the solid object is engulfed into the liquid in such a way that when the liquid moves, the solid object moves at the same general velocity as the fluid without adhering to the non-moving surface. In order to accomplish this, the liquid must have a low interfacial tension with the solid object. This is achieved through the use of surface active agents, as described below.

Increased viscosity and increased density contribute to a greater motive force for a liquid to impel a solid object through the mouth and down the throat. Further, increased viscosity allows a fluid to coat the surfaces of the mouth to provide a pleasant feeling in the mouth. However, the viscosity should not be increased to such a great extent that the oral delivery composition itself becomes difficult or uncomfortable to swallow.

Increased lubricity and increased viscosity of a liquid creates a boundary layer between a solid object and surfaces of the mouth, tongue, throat or esophagus so that a solid object can slide down the throat without becoming stuck. The forces that act upon a solid object that is moving in a fluid close to a surface, and the creation of a boundary layer are schematically illustrated in FIG. 1. As shown in FIG. 1, in a liquid 10 that is moving over a surface 20, the region of the liquid 30 that is farthest away from the surface has a freestream velocity, while the region of the liquid that is closest to the surface is affected by frictional drag (shown by reverse arrows) and has a zero velocity. In between is a boundary layer 40 in which the momentum transfer to zero velocity takes place. The creation of an effective boundary layer in a liquid that engulfs the tablet 50 serves to insure that the tablet does not transfer its momentum as it travels in the free stream, which would cause it to slow down and become stuck on the surface. Accordingly, the invention further relates to a method and composition for creating a boundary layer between a liquid that contains a solid object and a stationary surface in such a way that when the liquid moves, the solid object moves at the same general velocity as the liquid without adhering to the stationary surface. To accomplish this, the liquid must have a viscosity suitable to absorb the change in momentum from the stationary surface, where the velocity is close to zero, and the solid object, which has the velocity of the moving liquid. This is achieved through the use of viscosity building agents or thickening agents, as discussed below.

Preferred additives according to the present invention include, but are not limited to gelatin, thickening agents such as gums and starches, including, but not limited to natural and man-made thickeners such as guar, locust bean, tamarind, arabic, karaya, tragacanth, agar, algin, carrageenan, xanthan, celluloses, pectins, carboxylated algin, carboxymethyl cellulose, hydroxypropyl methyl cellulose, carboxylated pectin, carboxylated xanthan, sulfated carrageenen, sulfated furcellaran and gellan, surface active agents including non-ionic surface active agents, cationic surface active agents, anionic surface active agents and amphoteric surface active agents, liquid carbohydrates such as glycerine, polyglycols, sorbitols, corn syrups, and fructose syrups, lubricating agents such as dimethicone, castor oil, vegetable oil or other edible lubricants known in the art, and salt solutions such as phosphate salts.

In the present invention, it is not necessary that a single ingredient impart all of the changes in properties to the base liquid described herein. A combination of ingredients or additives, each contributing to change in a specific property of the base liquid, or a change in several specific properties, is within the scope of the invention.

Moreover, it is not necessary for the present invention that all of the described physical properties of the oral delivery composition be different from those of the base liquid. Oral delivery compositions are within the scope of the present invention if one or more of the physical properties are different from the properties of the base liquid so that when the oral delivery composition and a solid object to be swallowed by a user are administered together to the user and swallowed, the solid object is less likely to become lodged or stuck on tongue, throat, palate or esophageal surfaces of the user, in comparison to when the base liquid and the solid object are administered together and swallowed.

It is preferred that the base liquid for the composition be water, although any other consumable liquid, such as, for example, fruit juice, isotonic and artificially flavored drinks including carbonated or non-carbonated beverages can be used.

To provide the oral delivery composition of the present invention, the additive or additives that provide enhance physical properties as described above are mixed with the base liquid. Depending on the particular ingredients, the additive or additives may completely dissolve in the base liquid or may form a colloidal dispersion of additive particles, typically micron-sized or sub-micron-sized, in the base liquid.

Preferably, the oral delivery composition also includes sweeteners or flavoring agents to mask the taste of other ingredients of the delivery composition and/or the taste of the medications or dietary supplements or other materials that make up the solid object. Any flavoring agent, such as an artificial fruit flavor, can be added. A variety of flavoring agents are known for use in liquid oral medications, any of which can be used in the oral delivery composition of the present invention.

In another embodiment of the present invention, the oral delivery composition can also include one or more materials that provide a synergistic effect with a pharmaceutical agent or dietary supplement in the gastrointestinal tract. For example, oral delivery compositions may contain ingredients that increase or decrease the efficacy of the pharmaceutical agent or dietary supplement. Such a synergistic material can be selected depending on the desired effect and can be specific to the solid oral medication or dietary supplement, if necessary. For example, a synergistic material can be added to enhance the absorption of the medication or dietary supplement in the gastrointestinal tract or can be added to retard the absorption of the medication or dietary supplement in the gastrointestinal tract in the event a more controlled release of the medication or dietary supplement is desired.

Furthermore, as would be understood by one skilled in the art of pharmacology or pharmacodynamics, a vast array of other adjuvants to increase the efficacy of the delivery or the potency of the medication or dietary supplement or other solid materials could be added to enhance the observed effect in swallowing and/or to have a salutary effect in the gastrointestinal tract. These include, but are not limited to, dispersants, pH modifiers, anti-dispersants, side effect minimizers, synergistic agents, anti-nausea ingredients, anti-spasmodic ingredients, surfactants, etc., For ease of packaging and consumer use, the additive or additives of the oral delivery composition can be packaged without the base liquid. The additive or additives may be in the form of a liquid or a solid, such as, for example, a dry powder. The consumer would then mix the additive or additives with a base liquid (such as, for example, water or juice) to dissolve and/or emulsify the additive composition. The consumer would then use the solution/emulsion to assist in swallowing a solid object, such as a pill, capsule, caplet or tablet containing a pharmaceutical agent or dietary supplement, by placing the pill, capsule, caplet or tablet in the mouth and drinking a mouthful of the oral delivery composition.

The oral delivery composition may also be used when the pharmaceutical agent, dietary agent or other substance to be swallowed is in the form of particles. Here again, without the oral delivery composition of the present invention, there is a likelihood that the particles can get stuck onto surfaces of the mouth. The oral delivery composition prevents this from happening in the same way that it prevents a pill, capsule, tablet or caplet from becoming stuck.

Having described the invention, the following examples are given to illustrate specific applications of the invention, including the best mode now known to perform the invention. These specific examples are not intended to limit the scope of the invention described in this application.

EXAMPLES

Example 1

A test example of the oral delivery composition according to the present invention was prepared as follows. One 0.6 Oz. package of Strawberry JELL-O® brand gelatin dessert, sugar free, manufactured by Kraft Foods, Inc., Box SFGL, Rye Brook, N.Y. 10573, USA (containing gelatin, adipic acid, disodium phosphate, maltodextrin, fumaric acid, aspartame, artificial flavor, acesulfame potassium, salt, and Red 40) was dissolved in 1 cup of hot water. Two cups of ice cubes were added and the mixture was stirred.

Two MYLANTA® Gas Geltab Dose Maximum Strength tablets (125mg. per tablet) manufactured by Johnson & Johnson-Merck, Consumer Pharmaceutical Co., Fort Washington, Pa. 19034 USA (containing simethicone and benzyl alcohol, butylparaben, calcium phosphate, castor oil, croscarmellose sodium, D&C red #28, D&C yellow #1 0, edetate calcium disodium, FD&C blue#1, FD&C red #40, gelatin, hydroxypropyl methylcellulose, methylparaben, microcrystalline cellulose, propylparaben, sodium laurel sulfate, sodium propionate, sorbitol, stearic acid, titanium dioxide) were cut in half and soaked in one quarter cup of water until the active had gone into solution. The skins of the tablet which remained were discarded. This mixture was added to the gelatin mixture and stirred briefly. The result was allowed to sit in a glass bowl for about 30 minutes. After 30 minutes it was observed that the mixture was not gelatinous but more viscous than water.

RITE-AIDE® aspirin was the first test tablet. First an aspirin tablet was taken by an adult test subject with water and with some degree of difficulty (sticking to tongue). Fifteen minutes later another tablet of the same size was taken by the same adult test subject with the oral delivery composition according to the present invention prepared above. The test example of the oral delivery composition according to the present invention was pleasant tasting, slightly denser than water, and the result was that the tablet was taken with no difficulty whatever. This procedure was then repeated with a 25mg. BENADRYL® gelcap with sequence reversed, i.e., the gelcap first taken with the test example of the oral delivery composition according to the present invention and then taken with water with the same result; that is, the test example of the oral delivery composition according to the present invention was pleasant tasting, slightly denser than water, and the result was that the BENADRYL® gelcap was taken with no difficulty whatever. However, when taken with water, the BENADRYL® gelcap was taken with some degree of difficulty (sticking to the tongue).

The procedure was repeated with a sixteen year old test subject with the same results.

Example 2

A test example of an additive formulation for an oral delivery composition according to the present invention was made by combining Methocel K100M® (a high viscosity hydroxypropyl methylcellulose polymer available from Dow Chemical, Midland, Mich., USA), potassium sorbate, Tween 80® (polyoxyethylene sorbitan monooleate, available from ICI American Inc., Wilmington, Del., Michigan), an anti-foam agent (a simethicone emulsion from Witco Chemical Corporation, Houston, Tex., USA), a sweetener blend (3 parts sucralose and 2 parts acesulfame K), raspberry flavor (product #13429A from USF) and purified water. The specific ingredients of the additive formulation, and their relative amounts are as follows:

| | |
|---|---|
| Methocel K100m | 1.116% |
| Potassium Sorbate | 0.093% |
| Tween 80 | 0.126% |
| Antifoam Agent OSI | 0.061% |
| Sweetener Blend | 0.133% |
| Raspberry Flavor | 0.145% |
| Purified Water | 98.326% |

The additive formulation was diluted with water or fruit juice at various concentrations and the resulting oral delivery compositions were tested for their ability to facilitate the swallowing of a test capsule. It was found that oral delivery compositions diluted with water or fruit juice to about 10 to about 40%, particularly to about 20% to about 30%, performed the best. In particular, compositions with a dilution of between 20% and 30%, most preferably, 25%, in addition to facilitating the swallowing of a test pill, provided a pleasant mouth feel, a rich/smooth coating in the mouth and greater lubricity after swallowing the pill, particularly in the esophageal area.

The viscosity of oral delivery compositions of the above formulation at various dilutions was determined using a Rheometrics Scientific RFS-II rheometer with couette geometry. Samples were tested immediately after preparation following gentle manual stirring. The juice used in the study was Safeway Select Winners Thirst Quencher Tropical Punch® (32 fl oz.) with cap code 19:04 CT09-7 (Best Buy:March 2001). The de-ionized water (CAS 7732-18-5) was Thomas Scientific Cat # C864-746, Lot #1152-04, filtered through a 0.2 micron filter. The viscosity findings are summarized in the following Table 1:

TABLE 1

| Concentration of Additive (wt %) | Base liquid | Viscosity (mPa-s) | Temperature (° C.) |
|---|---|---|---|
| 10% | Juice | 2.1/2.1 | 36.9/37.0 |
| 20% | Juice | 3.4/3.4 | 37.0/37.0 |
| 30% | Juice | 14.2/14.4 | 36.8/36.8 |
| 10% | De-Ionized Water | 1.8/1.8 | 36.9/36.9 |
| 20% | De-Ionized Water | 4.6/4.6 | 37.0/36.8 |
| 30% | De-Ionized Water | 11.5/11.5 | 37.0/37.1 |

Example 3

An oral delivery composition suitable for scaled-up production was made with following formula:

| Item # | Ingredient | % by weight |
|---|---|---|
| 1 | Methocel K100 M ® | 0.301 |
| 2 | 25% potassium sorbate/sodium benzoate solution | 0.122 |
| 3 | Tween 80 ® | 0.034 |
| 4 | Simethecone suspension solution | 0.017 |
| 5 | 50X cranberry/raspberry flavor | 1.460 |
| 6 | potable water | 98.066 |

The oral delivery composition was prepared as follows:
1. Items 2,3,4 and 6 are pre-weighed and mixed in a sealable stream-jacketed tank or vessel. The mixture is heated to 185–200° F.
2. While stirring, the previously weighted item 1 is added to the mixing tank. The temperature is maintained between 185–200° F. (just below the boiling point of water.) and the mixture is stirred for at least five minutes. The cover is closed to prevent water loss. The stirring and heating serves to pasteurize the mixture and to disperse the cellulose with no lump or undissolved gum (fish eye) forming.
3. The solution is then cooled to about 150° F. The flavoring agent is added and the solution is mixed for an additional 2 minutes with the cover closed to prevent flavor flash off.
4. Sealable containers, such as bottles, are then filled with the hot solution (about 145° F. or lower). It is recommended that the filling step not be carried out above 150° F. because methocel has a gelling temperature of about 150° F. and carrying out the filling step above the gelling temperature may cause precipitation and uneven filling in the bottle. The containers are sealed and stored in a cool environment.

Under normal sealed conditions, the oral delivery composition should have a stable shelf life, in terms of color, flavor profile, viscosity and microbial counts, of at least 18–24 months.

Example 4

The following procedure provides a useful simulation of conditions in the mouth during the process of swallowing and allows for the testing of oral delivery compositions to determine whether a composition allows a tablet to flow with a fluid or causes the tablet to adhere to a surface: A single aspirin tablet is placed in a new, clean, dry 4 oz polypropylene sample jar. 10 cc of test fluid is measured out in a 25 ml graduated cylinder. On a lab bench, the fluid is quickly poured into the sample jar containing the aspirin, and immediately, the jar is lifted and inverted. If the tablet flows out with the fluid, the test is considered a success. If the tablet remains in the jar (for example, if it sticks to a surface of the jar), the test is considered a failure. The test can be carried out simultaneously with a test fluid and a control fluid such as de-ionized water to determine whether a test fluid performs better than the control fluid over multiple runs.

Using this procedure, tests were run on a 25% solution (in de-ionized water) of the additive formulation of Example 2. Grand Union uncoated 325 mg aspirin tablets were used as the test tablet. Out of 16 runs with the test formulation, 14 were successes and 2 were failures. By contrast, out of 16 runs with de-ionized water alone, 2 were successes and 14 were failures.

Example 5

An improved procedure for testing oral delivery compositions using 100 ml Pyrex® volumetric flasks. These flasks provide a hydrophilic surface and a long discharge channel when inverted. The throat of the flask has a small diameter, about 1 cm.

The testing procedure is as follows:

The flask is cleaned with de-ionized water.

10 ml of test solution is added to the flask.

The flask is capped and the interior of the flask is coated with the solution.

A test pill (tablet, caplet, gelcap, etc.) is added.

The solution is gently swirled by hand.

The flask is inverted and it is determined whether the pill has been evacuated.

This test procedure provides a visual demonstration of the effectiveness of a test solution as an oral delivery composition. In tests that were run following this procedure, when de-ionized water was used as the test solution, in most cases, the tablets, caplets and gel caps stuck to the sides of the flask and could not be discharged, even with significant mechanical energy input such as hard shaking or hitting on a hard surface. This was true even for coated pills. The pills had to be manually dislodged with a long flexible spatula.

When tests were run using a 25% (wt.)solution of the additive formula of Example 2 in cranberry/raspberry flavor diet Snapple® (a non-carbonated flavored drink), almost all pills could be emptied from the flask by simply inverting the flask.

The following is a summary of the test results:

| Solution | # of pass | # of fail |
|---|---|---|
| test pill: Bayer Toleraid Microcoating | | |
| de-ionized water | 0 | 10 |
| 25% solution of additive/Snapple ® | 10 | 0 |
| test pill: Finast ® Extra Strength Acetamenophen | | |
| de-ionized water | 0 | 10 |
| 25% solution of additive/Snapple ® | 9 | 1 |
| test pill: Motrin IB ® | | |
| de-ionized water | 0 | 10 |
| 25% solution of additive/Snapple ® | 10 | 0 |

The above tests dramatically show that an oral delivery composition that contains about 25% of the additive formula of Example 2, when mixed with a commercial flavored drink, prevents adhesion of various different types of pills and tablets to a hydrophillic surface. Also, the viscosity agents in the composition appear to apply a lubricious slippery surface to the flow channel, enabling the solid tablet, caplet or gel cap to be expelled.

Obviously, many modifications and variations of the present invention are possible in light of the above teachings. It is therefore to be understood that, within the scope of the appended claims, the invention may be practiced otherwise than as specifically described.

I claim:

1. An oral delivery composition for facilitating the swallowing of a solid object by a user, the oral delivery composition comprising:
    a mixture of a base liquid and at least one additive, wherein the at least one additive is selected and is present in the oral delivery composition in a sufficient concentration such that the oral delivery composition has the following properties:
    (1) a density that is greater than the density of the base liquid,
    (2) a surface tension that is less than the surface tension of the base liquid,
    (3) a viscosity that is greater than the viscosity of the base liquid,
    (4) a wettability that is greater that the wettability of the base liquid,
    (5) a lubricity that is greater than the lubricity of the base liquid, and
    (6) a lower interfacial tension than the interfacial tension of the base liquid,
such that when the oral delivery composition and the solid object are administered together to a user and swallowed, the solid object is less likely to become lodged or stuck on tongue, throat, palate or esophageal surfaces of the user, in comparison to when the base liquid and the solid object are administered together and swallowed.

2. The oral delivery composition of claim 1 wherein the base liquid comprises water.

3. The oral delivery composition of claim 1 wherein the base liquid comprises a fruit juice.

4. The oral delivery composition of claim 1 wherein the additive comprises a thickening agent and a surfactant.

5. The oral delivery composition of claim 4 wherein the thickening agent is selected from the group of gums and starches consisting of guar, locust bean, tamarind, arabic, karaya, tragacanth, agar, algin, carrageenan, xanthan, celluloses, pectins, carboxylated algin, carboxymethyl cellulose, hydroxypropyl methyl cellulose, carboxylated pectin, carboxylated xanthan, sulfated carrageenen, sulfated furcellaran and gellan.

6. The oral delivery composition of claim 4 wherein the surfactant is selected from the group of surface active agents consisting of non-ionic surface active agents, cationic surface active agents, anionic surface active agents and amphoteric surface active agents.

7. The oral delivery composition of claim 1 wherein the oral delivery composition further contains at least one of sweeteners and flavors.

8. The oral delivery composition of claim 1 wherein the oral delivery composition comprises water, carboxymethyl cellulose and a polysorbate surfactant.

9. The oral delivery composition of claim 1 wherein the solid object is a particle of food.

10. The oral delivery composition of claim 1 wherein the solid object is a pill, capsule, caplet or tablet containing a pharmaceutical agent or food supplement in unit dosage form.

11. The oral delivery composition of claim 1 wherein the solid object comprises a plurality of solid particles.

12. An oral delivery composition comprising:
    a mixture of a base liquid, a water soluble cellulosic polymer and a surface active agent, wherein the water soluble cellulosic polymer and the surface active agent are present in the oral delivery composition in a sufficient concentration such that the oral delivery composition has improved physical properties, in comparison with the base liquid, such that when the oral delivery composition and a solid object to be swallowed by a user are administered together to the user and swallowed, the solid object is less likely to become lodged or stuck on tongue, throat, palate or esophageal surfaces of the user, in comparison to when the base liquid and the solid object are administered together and swallowed.

13. The oral delivery composition of claim 12 wherein the water soluble cellulosic polymer is carboxymethyl cellulose and the surface active agent is polyoxyethylene sorbitan monooleate.

14. An additive for an oral delivery composition that includes a base liquid and the additive, comprising:
    at least one substance that, when combined with the base liquid, provides an oral delivery composition having the following properties:
    (1) a density that is greater than the density of the base liquid,
    (2) a surface tension that is less than the surface tension of the base liquid,
    (3) a viscosity that is greater than the viscosity of the base liquid,
    (4) a wettability that is greater that the wettability of the base liquid, (5) a lubricity that is greater than the lubricity of the base liquid, and (6) a lower interfacial tension than the interfacial tension of the base liquid, such that when the oral delivery composition and the solid object are administered together to a user and swallowed, the solid object is less likely to become lodged or stuck on tongue, throat, palate or esophageal surfaces of the user, in comparison to when the base liquid and the solid object are administered together and swallowed.

15. The additive of claim 14 wherein the additive, before it is combined with the base liquid, is in the form of a dry powder.

16. A method for swallowing of a solid object by a user, the method comprising the steps of:

providing an oral delivery composition comprising a mixture of a base liquid and at least one additive, wherein the at least one additive is selected and is present in the oral delivery composition in a sufficient concentration such that the oral delivery composition has the following properties:

(1) a density that is greater than the density of the base liquid, (2) a surface tension that is less than the surface tension of the base liquid, (3) a viscosity that is greater than the viscosity of the base liquid, (4) a wettability that is greater that the wettability of the base liquid, (5) a lubricity that is greater than the lubricity of the base liquid, and (6) a lower interfacial tension than the interfacial tension of the base liquid, such that when the oral delivery composition and the solid object are administered together to a user and swallowed, the solid object is less likely to become lodged or stuck on tongue, throat, palate or esophageal surfaces of the user, in comparison to when the base liquid and the solid object are administered together and swallowed, and administering the solid object and the oral delivery composition together to the user.

17. The method of claim 16 wherein the base liquid comprises water.

18. The method of claim 16 wherein the base liquid comprises a fruit juice.

19. The method of claim 16 wherein the additive comprises a thickening agent and a surfactant.

20. The method of claim 19 wherein the thickening agent is selected from the group of gums and starches consisting of guar, locust bean, tamarind, arabic, karaya, tragacanth, agar, algin, carrageenan, xanthan, celluloses, pectins, carboxylated algin, carboxymethyl cellulose, hydroxypropyl methyl cellulose, carboxylated pectin, carboxylated xanthan, sulfated carrageenen, sulfated furcellaran and gellan.

21. The method of claim 19 wherein the surfactant is selected from the group of surface active agents consisting of non-ionic surface active agents, cationic surface active agents, anionic surface active agents and amphoteric surface active agents.

22. The method of claim 16 wherein the oral delivery composition further contains at least one of sweeteners and flavors.

23. The method of claim 16 wherein the oral delivery composition comprises water, carboxymethyl cellulose and a polysorbate surfactant.

24. The method of claim 16 wherein the solid object is solid object is a pill, capsule, caplet, tablet or any medicinal solid containing a pharmaceutical agent or food supplement in unit dosage form.

25. The method of claim 16 wherein the solid object is a pill, capsule, caplet or tablet containing a pharmaceutical agent or food supplement in unit dosage form, wherein the pill, capsule, caplet or tablet is elongated in one dimension and wherein, when the elongated pill, capsule, caplet or tablet is administered to a user together with the oral delivery composition, the oral delivery composition exerts a force on the elongated pill, capsule, caplet or tablet to cause the elongated pill, capsule or tablet to line up axially with the throat passage of the user.

26. The method of claim 16 wherein the solid object comprises a plurality of solid particles.

27. The method of claim 16 wherein the solid object is a pill, capsule, caplet or tablet containing a pharmaceutical agent or food supplement in unit dosage form, wherein the pill, capsule, caplet or tablet comprises a material that has a tendency to crumble or dissolve when exposed to water or natural fluids in the mouth of the user, and wherein, when the pill, capsule or tablet is administered to a user together with the oral delivery composition, the oral delivery composition facilitates the swallowing of the pill, capsule, caplet or tablet before crumbling or dissolving of the pill, capsule, caplet or tablet can occur in the mouth of the user.

28. A method for swallowing a solid object by a user, the method comprising the steps of:

providing an oral delivery composition comprising a mixture of a base liquid, a water-soluble cellulosic polymer and a surface active agent, wherein the water soluble cellulosic polymer and the surface active agent are present in the oral delivery composition in a sufficient concentration such that the oral delivery composition has improved physical properties, in comparison with the base liquid, such that when the oral delivery composition and the solid object are administered together to a user and swallowed, the solid object is less likely to become lodged or stuck on tongue, throat, palate or esophageal surfaces of the user, in comparison to when the base liquid and the solid object are administered together and swallowed administering the solid object and the oral delivery composition together to a user.

29. The method of claim 28 wherein the water soluble cellulosic polymer is carboxymethyl cellulose and the surface active agent is polyoxyethylene sorbitan monooleate.

30. A method for swallowing of a solid object by a user, the method comprising the steps of:

providing an oral delivery composition comprising a liquid having the following properties:

a viscosity that provides buoyancy to the solid object and a wettability that allows the solid object to be engulfed by the liquid oral delivery composition wherein the viscosity and wettability are selected such that when the oral delivery composition and the solid object are administered together to a user and swallowed, the solid object is engulfed by the liquid and carried along a barrier layer created due to the viscosity of the liquid so that the solid object floats through the liquid and does not become lodged or stuck on tongue, throat, palate or esophageal surfaces of the user, and administering the solid object and the oral delivery composition together to the user.

31. The method of claim 30 wherein the viscosity is greater than 3.5 mPa-s at 37° C.

32. The method of claim 30 wherein the oral delivery composition comprises a base liquid and one or more additives, wherein the additive or additives, alone or in combination have the properties of a thickening agent and a surfactant.

33. The method of claim 32 wherein the thickening agent is selected from the group of gums and starches consisting of guar, locust bean, tamarind, arabic, karaya, tragacanth, agar, algin, carrageenan, xanthan, celluloses, pectins, carboxylated algin, carboxymethyl cellulose, hydroxypropyl methyl cellulose, carboxylated pectin, carboxylated xanthan, sulfated carrageenen, sulfated furcellaran and gellan.

34. The method of claim 32 wherein the surfactant is selected from the group of surface active agents consisting of non-ionic surface active agents, cationic surface active agents, anionic surface active agents and amphoteric surface active agents.

35. The method of claim 32 wherein the surfactant is a polysorbate surfactant.

36. The method of claim 32 wherein the thickening agent is carboxymethyl cellulose and the surfactant is polyethylene sorbitan monooleate.

37. An oral delivery composition for facilitating the swallowing of a plurality of solid particles by a user, the oral delivery composition comprising:
   a mixture of a base liquid and at least one additive, wherein the at least one additive is selected and is present in the oral delivery composition in a sufficient concentration such that the oral delivery composition has the following properties:
   (1) a density that is greater than the density of the base liquid,
   (2) a surface tension that is less than the surface tension of the base liquid,
   (3) a viscosity that is greater than the viscosity of the base liquid,
   (4) a wettability that is greater that the wettability of the base liquid,
   (5) a lubricity that is greater than the lubricity of the base liquid, and
   (6) a lower interfacial tension than the interfacial tension of the base liquid,
such that when the oral delivery composition and the plurality of solid particles are administered together to a user and swallowed, the solid particles are less likely to become lodged or stuck on tongue, throat, palate or esophageal surfaces of the user, in comparison to when the base liquid and the solid particles are administered together and swallowed.

38. A method for swallowing of a plurality of solid particles by a user, the method comprising the steps of:
   providing an oral delivery composition comprising a mixture of a base liquid and at least one additive, wherein the at least one additive is selected and is present in the oral delivery composition in a sufficient concentration such that the oral delivery composition has the following properties:
   (1) a density that is greater than the density of the base liquid,
   (2) a surface tension that is less than the surface tension of the base liquid,
   (3) a viscosity that is greater than the viscosity of the base liquid,
   (4) a wettability that is greater that the wettability of the base liquid,
   (5) a lubricity that is greater than the lubricity of the base liquid, and
   (6) a lower interfacial tension than the interfacial tension of the base liquid,
such that when the oral delivery composition and the plurality of solid particles are administered together to a user and swallowed, the solid object is less likely to become lodged or stuck on tongue, throat, palate or esophageal surfaces of the user, in comparison to when the base liquid and the solid particles are administered together and swallowed, and
   administering the solid particles and the oral delivery composition together to the user.

39. A method for swallowing of a solid particles by a user, the method comprising the steps of:
   providing an oral delivery composition comprising a liquid having the following properties:
   a viscosity that provides buoyancy to the solid particles and
   a wettability that allows the solid particles to be engulfed by the liquid oral delivery composition
   wherein the viscosity and wettability are selected such that when the oral delivery composition and the solid particles are administered together to a user and swallowed, the solid particles are engulfed by the liquid and carried along a barrier layer created due to the viscosity of the liquid so that the solid particles float through the liquid and do not become lodged or stuck on tongue, throat, palate or esophageal surfaces of the user, and
   administering the solid particles and the oral delivery composition together to the user.

* * * * *